United States Patent [19]

Maggio

[11] 4,397,956

[45] Aug. 9, 1983

[54] MEANS FOR MONITORING THE STATUS OF CONTROL OF KETOACIDOSIS-PRONE DIABETICS

[76] Inventor: Edward T. Maggio, 12588 Chetenham La., San Diego, Calif. 92128

[21] Appl. No.: 329,392

[22] Filed: Dec. 10, 1981

[51] Int. Cl.$^3$ .................. G01N 33/52; G01N 33/64; G01N 33/66
[52] U.S. Cl. ......................................... 436/34; 422/56; 436/95; 436/128; 436/130; 436/131
[58] Field of Search ........... 422/56; 23/230 R, 230 B; 436/34, 95, 128, 130, 131

[56] References Cited

U.S. PATENT DOCUMENTS

| | | | |
|---|---|---|---|
| 3,915,644 | 10/1975 | Walraven | 436/34 |
| 3,954,412 | 5/1976 | Ogawa | 436/128 X |
| 4,147,514 | 4/1979 | Magers | 422/56 X |
| 4,160,646 | 7/1979 | Furutani | 23/230 R |
| 4,336,330 | 6/1982 | Bauer | 422/56 X |

OTHER PUBLICATIONS

Chemical Abstracts, 95: 22453p (1981).

Primary Examiner—Sidney Marantz

[57] ABSTRACT

Method and test system for monitoring the status of control of ketoacidosis-prone diabetics using pseudo-kinetic methods. Pseudo-kinetic clinical information is obtained by analysis of a single blood sample in which the blood glucose level is determined along with one or more additional indicator analytes present in patient blood, serum or plasma. The additional indicator analyte(s) provide a "historical" picture of recent events within the patient relating to glucose metabolism which, when analyzed in conjunction with the blood glucose level, provides, from a single sample, a holistic view of the degree of metabollic control in the diabetic patient which is otherwise obtainable at the present time only by the much less desirable process of drawing and analyzing multiple samples over a period of time. The additional indicator analyte may be ketone bodies.

8 Claims, 3 Drawing Figures

KEY:  N = NORMAL
H = HIGHER THAN NORMAL
L = LOWER THAN NORMAL
↑ = INCREASING
↓ = DECREASING
→ = FLAT

MEANS FOR MONITORING THE STATUS OF CONTROL OF KETOACIDOSIS-PRONE DIABETICS

BRIEF SUMMARY OF THE INVENTION

This invention relates to a means for monitoring the status of the control of ketoacidosis-prone diabetics using pseudo-kinetic methods. It also relates to test systems comprising reagents and instrumentation relating to such means.

BACKGROUND OF THE INVENTION

Diabetes Mellitus is a disorder of the carbohydrate metabolism characterized by abnormal insulin secretion. Depending upon the degree of insulin secretion impairment, diabetics are classified as either ketoacidosis-prone or ketoacidosis-resistant. These classifications are also known as juvenile-onset or insulin-dependent and maturity-onset or non-insulin dependent, respectively. In some cases, insulin-dependent or ketoacidosis-prone diabetics are difficult to manage. Such patients are often called "brittle" diabetics and occasionally such patients must be hospitalized in order to determine their insulin requirements and in effect stabilize their condition.

Even in the above situation where a patient is hospitalized and/or subsequently stabilized, the long-term results of such abnormal insulin/glucose blood levels are serious physical impairments such as retinapathy, neuropathy and other serious clinical manifestations.

In the past, screening methods such as the determination of the presence of abnormal levels of glucose and ketone-bodies in the urine were also used to monitor the condition of the status of control of diabetic patients. Such methods were used because of the availability of simplified test reagents such as paper strips impregnated with reagents and the non-invasive nature of the urine sample being tested. Such methods are very unsatisfactory since by the time the glucose spills over into the urine, the patient is usually well out of control.

More recently, methods have been developed which involve the determination of glucose levels in blood as a measure of the status of control of a diabetic patient. Such methods initially involved laboratory procedures since the tests were conducted using plasma rather than whole blood. However, in the past two to three decades, methods have evolved using reagent strips which can be used with small amounts of whole blood, such as from droplettes of whole blood taken from a finger-tip puncture with a sterile lancet. Such methods, coupled with a simple, battery operated reflectance meter have opened entirely new testing vistas and have led to the concept of home testing by the diabetic himself. Thus, several tests can be conducted in a single day without unduly inconveniencing the patient and the attending physician.

Regardless of the above advances, present methods for assessing or monitoring the status of control of brittle diabetics is far from ideal. This is partially due to the fact that blood glucose levels may vary widely during the course of a few hours or less due to varying sugar intake and varying ability to metabolize glucose. Frequent blood glucose measurements are recommended. A simple blood sample provides only limited information regarding the success of the patient in controlling glucose levels. A single point glucose measurement provides limited information. FIG. 1 provides a hypothetical graph of blood glucose levels during the course of a day. Samples taken only at times $t_b$, $t_d$ and/or $t_f$ might erroneously suggest that the hypothetical patient in FIG. 1 is adequately controlled. Sampling at more frequent intervals, for example at time $t_a$ through $t_g$ inclusive, would yield a more complete picture suggesting that the patient is not well controlled at all, but in fact is cycling through high and low serum glucose levels during the course of the day. A patient may require that as many as eight or more blood samples be drawn daily in order that an adequate picture of blood glucose levels be obtained. Obtaining blood samples is an invasive process which is usually neither pleasant nor convenient. A means of obtaining additional information from a single blood sample which would either reduce the total number of samples needed to be drawn or allow for a clearer clinical picture to be drawn from such determinations would clearly be beneficial and valuable to the patient.

More recently, a method has been developed which overcomes some of the above noted testing deficiencies. This new method is based on the finding that the glycosylated fractions of hemoglobin A (HbA) are increased in diabetics in proportion to the level of elevation of blood glucose above normal. The glycosylated or "fast" hemoglobins are formed continuously in the red cell over its 120-day life span and it was found that the amount of the most abundant fraction $HbA_{lc}$ may double in diabetics which have not been adequately controlled over the period during which this fraction is formed. Thus a test for the determination of $HbA_{lc}$ is indicative of how well a diabetic has been controlled during the previous several months.

This test, although an advance in the art, is not entirely satisfactory since it is a complicated laboratory test and information is not obtained on a timely basis, i.e., the information is obtained only after about 2-3 months during which the diabetic may be considerably out of control and suffering the impairments described herein.

DESCRIPTION OF THE PRIOR ART

Methods and test devices previously used to control diabetics are described above. No direct prior art is known relating to the present invention, including its specific embodiments.

In the present invention, a means is disclosed for monitoring the status of control of ketoacidosis-prone or brittle diabetics using a pseudo-kinetic means. This means basically comprises measuring blood glucose and at least one additional indicator analyte in blood using appropriate clinical chemistry techniques. An indicator analyte is defined as an analyte present in a body fluid (e.g., blood, serum, plasma, tears) and whose concentration shows a change in concentration over an intermediate time frame (for example, 5 minutes to 12 hours, preferably 15 minutes to 3 hours) in response to changes in glucose metabolism. A variety of such analytes may be measured including but not limited to the following: ketone bodies such as acetone, β-hydroxybutyrate and acetoacetate and fatty acid derivatives.

Figure 2:
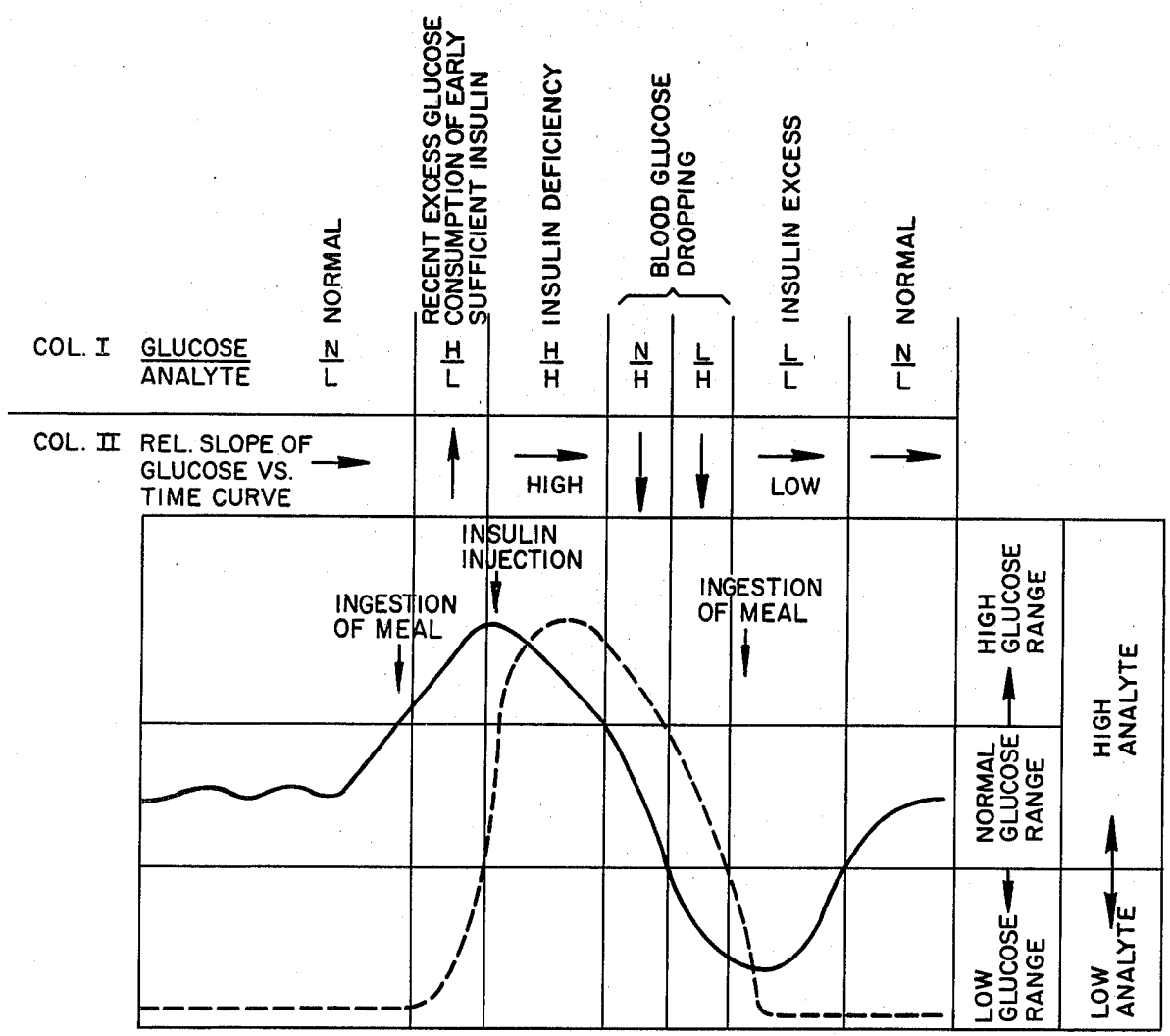
FIG. 2 is a chart showing the relationship of glucose and second analyte levels in an insulin-dependent diabetic patient.

During insulin deficiency, as may occur between therapeutic insulin injections as the result of metabolism of insulin, energy needed to sustain brain function cannot be derived sufficiently from glucose, the chief source of energy for the brain. In this situation, the fatty acid oxidation pathways are called upon to supply alternate energy sources to the brain. Byproducts from this metabolic process, including ketone bodies, fatty acid metabolites and the like, may be detected in blood and other body fluids when the fatty acid metabolizing pathways are activated. Since these analytes are not cleared from the blood immediately when the blood glucose level is restored to a normal level, they provide short or intermediate term "historical" information concerning the state of glucose metabolism in the patient. FIG. 2 illustrates the relationship of relative glucose levels to relative analyte levels (Column I) and how the relationship, obtained from any given single measurement, indicates the relative slope of the glucose vs. time curve for the time period surrounding the single point measurement. It can be seen that a single sampling of blood can yield pseudo-kinetic information about blood glucose levels as well as a simple concentration level.

More specifically, the present invention utilizes techniques which can be adapted to simplified-appearing test devices. Such devices which on the surface appear to be simple, are technically extremely sophisticated and may comprise solid state reagent strips and instruments to "read" such strips, although other methodologies, such as lyophylized reagents in miniature cuvettes may also be used.

The preferred reagents of the present invention comprise a solid matrix, such as paper or a polymer into which suitable reagents are impregnated or included. Such reagents upon being contacted by glucose or a second analyte change color, or alter fluorescence, depending upon the concentration of the substance in the body fluid.

Since the present invention may advantageously be used in a home environment by the patient himself, as will be described later, the preferable body fluid is whole blood taken from a finger or earlobe puncture.

In order to avoid the use of separation techniques and so that the red hemoglobin of the whole blood does not obscure the color reaction, the surface of the paper matrix containing the reagents is coated with a semi-permeable water insoluble membrane which in effect screens out the red blood cells but allows the glucose or analyte to pass through and contact the reagents. If a polymeric matrix is used, the membrane may be avoided since the polymer may itself act as a membrane to screen out the red cells and allow the substance being detected to contact the reagent entrapped in the membrane.

Figure 1:
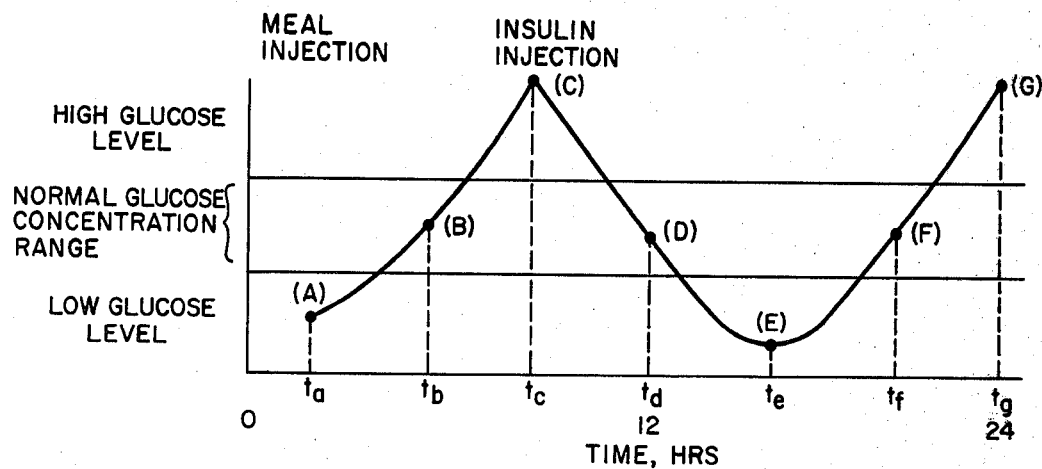
FIG. 1 is a chart showing blood glucose levels for an insulin-dependent diabetic patient and the lack of control thereof.
Figure 3:
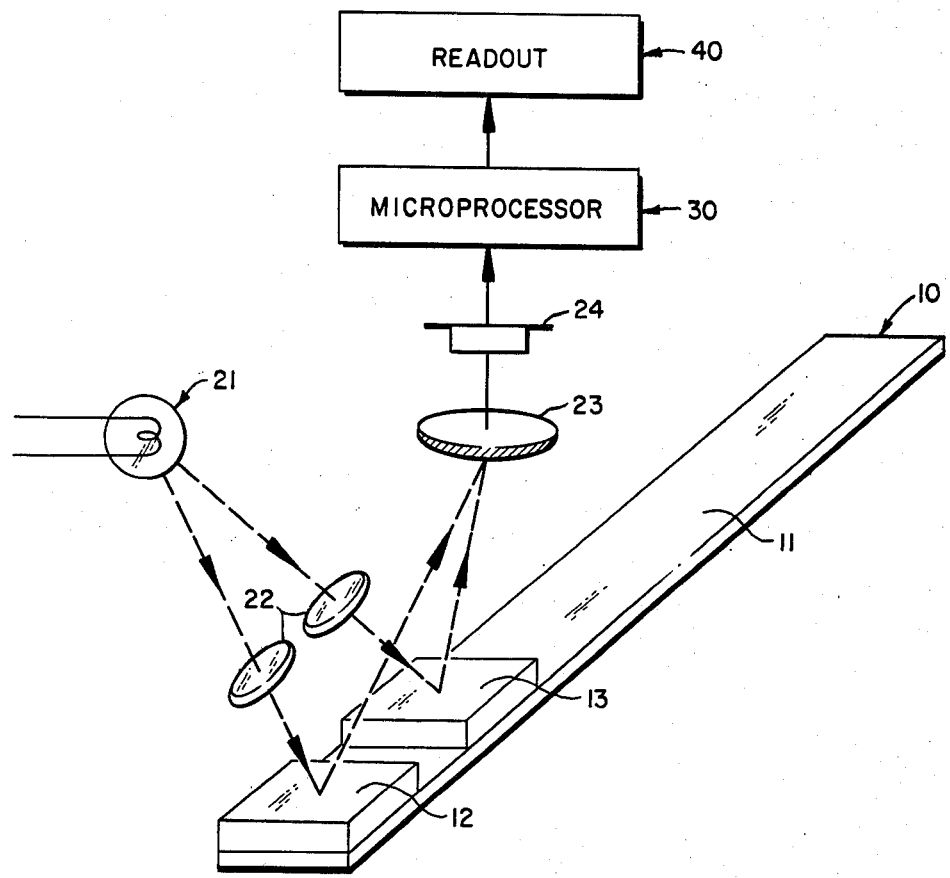
FIG. 3 is a block diagram of a test system which may be used in the present invention.

The construction of the preferable test devices of the present invention are shown in FIG. 3, wherein 10 is a test reagent strip device having two reagent impregnated paper pads 12 and 13 attached thereto. Twelve is a glucose test reagent pad and 13 is a ketone test reagent pad. In use a light source (21) from a suitable power supply is passed through filters (22) and impinge on pads 12 and 13. Depending on the color of such pads, 12 and 13, light is reflected away, passes through shutter 23 which separates such reflected radiation into its component parts which is measured by light detector 24. The energy from detector 24 is analyzed by microprocessor 30 which in turn instructs readout 40 to display the data for visual inspection.

It is preferable, but by no means absolutely necessary, that the color developed in the reagent device be read by instrumental means. However, in certain instances ultraviolet radiation may be absorbed or reflected by the products of chemical reaction of the substance contacting the glucose or second analyte and in such instances an instrument must be employed.

Since the present invention is advantageously used in a home testing situation, the instrument used should have certain features such as portability (battery operated), digital readout, simplified operation, a readout timer, and so forth. When reagent strips are used as the test reagents, the instrument will be a reflectance type device and the two or more reagents may be read simultaneously or sequentially. State of the art electronics also allows for the use of a microprocessor for controlling the instrument performance and interpreting the test results obtained thereby. The instrument should also have a memory whereby previous results are retained and used to interpret the status of control of the patient. An algorithm may be used as an analyzing means which considers the glucose concentration level, the second or additional indicator analyte concentration level and calculates the instantaneous determination of the slope of the change of the glucose concentration and in effect, using this pseudo-kinetic method, determines or monitors the status of control of the diabetic patient.

In a home testing environment it is very important that the results obtained be properly presented and retained for physician review. Although the patient may simply record the results in a daily diary, it is preferable that a printed record be maintained. This is advantageously accomplished by having a printed or magnetic card record which is inserted daily in the instrument and presents the results in a logical, facile manner.

Results obtained should at least include glucose concentration, second analyte concentration and an interpretive indication of the status of patient control such as, for example, a printed statement at the end of the day that the patient was "in proper control during the previous 24-hour period".

Although an instrument is preferable, it may be that health care costs would prevent universal use of such a device. In such an instance, a visual readout may be used and an inexpensive slide rule type of interpretative device utilized to indicate the status of control. Moreover, in a hospital or clinical environment, much more sophisticated readout devices may be utilized.

EXAMPLE

Preparation of Reagent Strips

1. Glucose Test Reagent—Sheets of Eatman and Dikeman filter paper number 641 are saturated with the following solution:
   Sodium Alginate: 5.0 g
   Polyoxyethylene Sorbital Monoleate (1% solution): 50.0 ml
   Gelatin: 12.0 g
   o-Tolidine.2HCl: 2.5 g
   Buffer comprising aqueous solution of:
     22.2 g citric acid and
     97.8 g sodium citrate: 300.0 ml
   Glucose Oxidase: 18.2 g Horseradish Peroxidase: 380.0 mg
Ethanol (95%): 125.0 ml The sheets are dried at 100° C. for 15 minutes, dipped into a 2% (vol/vol) solution of cellulose acetate in acetone, air dried for about an hour, and cut into 0.5 cm squares.

2. Ketone Test Reagent—Sheets of Eatman and Dikeman filter paper number 641 are first dipped into a solution comprising:

Glycine: 10.0 g
Sodium Nitroprusside: 0.5 g
Sodium chloride: 10.0 g
Monosodium Phosphate-Monohydrate: 23.8 g
Disodium Phosphate-Anhydrous: 1.25 g
Distilled water, Q.S. to: 100.0 ml and then dried at 100° C. for about 15 minutes. The sheets are then dipped into a solution comprising:

1,3-diamino-2-propanol: 10.0 g
2-amino-2-methyl-1,3-propanediol: 20.0 g
Absolute ethanol, Q.S. to: 100.0 ml and dried at about 50° C. for an additional 10 minutes. Subsequently, the sheets are dipped into a 2% solution of cellulose acetate in acetone, air dried for about an hour and cut into squares 0.5 cm on edge.

3. Fabrication of Test Reagent Device—The glucose test reagent squares are affixed to the end of strips of sheet polyethylene about 0.025 cm thick, 10 cm long by 0.5 cm wide. Ketone test reagent squares were affixed to the same strips but positioned about 3 mm above the glucose strips. The result is test device 10 shown in FIG. 3.

Use of Test Devices

The test devices described above are used by brittle diabetic patients under a physician's instructions in a home situation to monitor the status of control afforded them by their insulin regime as follows:

A drop of whole blood from a finger puncture sample is placed on each of the test reagents and allowed to remain there for one minute after which it is wiped or washed off in a stream of cold water. The strip is immediately placed in a readout instrument as described herein, the results interpreted by the instrument and a daily printed readout obtained for physician review.

What is claimed is:

1. A method for monitoring the status of control of ketoacidosis-prone diabetics comprising measuring, on a single body fluid sample, the concentration levels of glucose and at least one additional indicator analyte, the additional indicator analyte being present in the body fluid in response to changes in the glucose metabolism of the diabetic within from about 5 minutes to about 12 hours of such change, and using the measured concentration level of the additional indicator analyte in conjunction with the measured concentration level of the glucose to calculate the instantaneous determination of the slope of the change of the glucose concentration and consequently reporting on the status of control of the diabetic.

2. A method as in claim 1 wherein an algorithm is used to calculate the instantaneous determination of the slope of the change of the glucose concentration.

3. A method as in claim 1 wherein the body fluid is blood.

4. A method as in claim 1 wherein the additional indicated analyte is ketone bodies.

5. A test system for monitoring the status of control of ketoacidosis-prone diabetics comprising, in combination, a test means for measuring, on a single body fluid sample, the concentration levels of glucose and at least one additional indicator analyte, the additional indicator analyte being present in the body fluid in response to changes in the glucose metabolism of the diabetic within from about 5 minutes to about 12 hours of such change, and analyzing means for calculating the instantaneous determination of the slope of the change of the glucose concentration and reporting the status of control of the diabetic.

6. A test system as in claim 5 wherein the additional indicator analyte is ketone bodies.

7. A test system as in claim 5 wherein the body fluid is whole blood and the test means comprises reagent pads coated with a membrane and a reflectance meter to measure the response of the reagent pads to the presence of glucose and the additional indicator analyte.

8. A test system as in claim 5 wherein the analyzing means comprises an algorithm for calculating the instantaneous determination of the slope of the glucose concentration.

* * * * *